(12) United States Patent
Sévigny et al.

(10) Patent No.: US 9,046,495 B2
(45) Date of Patent: *Jun. 2, 2015

(54) NON-TOXIC SOLVENT FOR CHROMOGENIC SUBSTRATE SOLUTION AND USES THEREOF

(71) Applicant: Pierce Biotechnology, Inc., Rockford, IL (US)

(72) Inventors: Pierre Sévigny, Montréal (CA); Martina Bielefeld-Sévigny, Montréal (CA)

(73) Assignee: Pierce Biotechnology, Inc., Fair Lawn, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/958,867

(22) Filed: Aug. 5, 2013

(65) Prior Publication Data

US 2013/0316330 A1 Nov. 28, 2013

Related U.S. Application Data

(63) Continuation of application No. 10/533,544, filed as application No. PCT/CA03/01690 on Oct. 31, 2003, now Pat. No. 8,501,433.

(60) Provisional application No. 60/422,873, filed on Nov. 1, 2002.

(51) Int. Cl.
  *C12Q 1/04* (2006.01)
  *G01N 21/78* (2006.01)
  *C12Q 1/54* (2006.01)

(52) U.S. Cl.
  CPC ............... *G01N 21/78* (2013.01); *C12Q 1/045* (2013.01); *C12Q 1/54* (2013.01)

(58) Field of Classification Search
  None
  See application file for complete search history.

(56) References Cited

U.S. PATENT DOCUMENTS

| 4,596,770 A | 6/1986 | Parham et al. ................. 435/7.9 |
| 5,317,042 A | 5/1994 | Narayanan |
| 5,403,721 A | 4/1995 | Ward et al. ..................... 435/34 |
| 2002/0086278 A1 | 7/2002 | Gosnell et al. ................... 435/4 |

FOREIGN PATENT DOCUMENTS

| EP | 0 354 027 A | 2/1990 |
| EP | 0 410 655 A | 1/1991 |
| EP | 0 950 403 A | 10/1999 |
| WO | WO 94/13777 | 6/1994 |
| WO | WO 98/50566 A | 11/1998 |

*Primary Examiner* — Lisa J Hobbs
(74) *Attorney, Agent, or Firm* — Thompson Hine LLP

(57) ABSTRACT

The present invention relates to a non-toxic dipolar solvent for chromogenic substrate for detecting presence of lacZ gene and/or gene activity, which comprises a stabilizing amount of a solubilizing agent. The present invention also relates to a method for inducing lac operon in screening assay, comprising the step of contacting an agar plate with at least one essential oil in a concentration sufficient to induce the lac operon. The present invention further relates to a method for detecting the presence of bacteria, comprising the step of contacting an agar plate with at least one essential oil in a concentration sufficient to induce detection of the bacteria.

26 Claims, 4 Drawing Sheets

NON-TOXIC SOLVENT FOR CHROMOGENIC SUBSTRATE SOLUTION AND USES THEREOF

PRIORITY

This application claims priority to co-pending U.S. application Ser. No. 10/533,544, which claims priority to PCT/CA 03/01690 filed Oct. 31, 2003, which claims priority to U.S. application Ser. No. 60/422,873 filed Nov. 1, 2002 each of which is expressly incorporated by reference herein in its entirety.

BACKGROUND OF THE INVENTION (a) Field of the Invention

This invention relates to a non-toxic solvent for preparing chromogenic substrate solution and uses thereof.

(b) Description of Prior Art

Many of the cloning and expression vectors in current use (e.g. the pUC series) carry a short segment of E. coli DNA that contains the regulatory sequences and the coding information for the first 146 amino acids of the β-galactosidase gene (lacZ). Embedded in this coding region is a polycloning site that does not disrupt the reading frame but results in the harmless interpolation of a small number of amino acids into the amino-terminal fragment of β-galactosidase. Vectors of this type are used in host cells that code for the carboxy-terminal portion of β-galactosidase. Although neither the host-encoded nor the plasmid-encoded fragments are themselves active, they can associate to form an enzymatically active protein. This type of complementation, in which deletion mutants of the operator-proximal segment of the lacZ gene are complemented by β-galactosidase-negative mutants that have the operator-proximal region intact, is called α-complementation. The Lac+ bacteria that result from α-complementation are easily recognized because they form blue colonies in the presence of the chromogenic substrate 5-Bromo-4-chloro-3-indoxyl-β-D-galactopyranoside (X-gal) (Horwitz et al. 1964. Substrates for cytochemical demonstration of enzyme activity. I. Some substituted 3-indoxyl-β-D-galactopyranosides. J. Med. Chem. 7:574.). However, insertion of a fragment of foreign DNA into the polycloning site of the plasmid almost invariably results in the production of an amino-terminal fragment that is not capable of α-complementation. Bacteria carrying recombinant plasmids therefore form white colonies. The development of this simple color test has greatly simplified the identification of recombinants constructed in plasmid vectors of this type. It is easily possible to screen many thousands of colonies visually and to recognize colonies that carry putative recombinant plasmids. The structure of these plasmids is then verified by restriction analysis of mini-preparations of plasmid DNA.

To a pre-made LB agar plate containing the appropriate antibiotics, a quantity of a stock solution of X-gal (20 mg/ml in dimethylformamide (DMF) or Dimethyl sulfoxide (DMSO)) and a quantity of a solution of isopropylthio-β-D-galactoside (IPTG) is added. The stock solution of X-gal is usually prepared by dissolving X-gal in dimethylformamide or Dimethyl sulfoxide which is a toxic solvent presenting also the drawback of providing solutions that are not stable through time.

IPTG is an important addition to the blue-white screening. The vectors carrying a segment of DNA derived from the lac operon of E. coli that codes for the amino-terminal fragment of β-galactosidase can be induced by isopropylthio-β-D-galactoside (IPTG). Bacteria exposed to the gratuitous inducer IPTG synthesize both fragments of the enzyme and form blue colonies when plated on media containing the chromogenic substrate 5-Bromo-4-chloro-3-indoxyl-β-D-galactopyranoside (X-gal).

It would be highly desirable to be provided with new solvents that are non toxic for preparing chromogenic substrate solutions used in screening assays, these solvents providing an extended stability of the chromogenic substrate solution.

SUMMARY OF THE INVENTION

In accordance with the present invention there is provided a non-toxic dipolar solvent for chromogenic substrate for detecting presence of lacZ gene and/or lacZ gene activity, which comprises a stabilizing amount of a solubilizing agent.

The solvent in accordance with a preferred embodiment of the present invention, wherein the solvent is a microemulsion.

The solvent in accordance with a preferred embodiment of the present invention, wherein the solubilizing agent is at least one selected from the group consisting of 1-Methylpyrrolidone (NMP), N'-dimethyl propylene urea (DMPU), Propylene carbonate (PC) and essential oil.

The solvent in accordance with a preferred embodiment of the present invention, wherein the essential oil is present in an effective solubilizing concentration for dissolving the chromogenic substrate.

The solvent in accordance with a preferred embodiment of the present invention, wherein the essential oil is selected from the group consisting of *Abies alba, Aniba roseodora, Cedrus atlantica, Citrus aurantifolia, Citrus aurantium, Citrus bergamia, Citrus limon, Citrus paradisi, Citrus reticulata, Citrus sinensis, Cupressus sempervirens, Juniperus communis, Juniperus virginiana, Picea mariana, Pinus sylvestris, Ravensara aromatica, Rosmarinus officinalis*, citrus extracts, pine terpenoids, conifers extracts, limonene oil and linseed oil.

In accordance with the present invention, there is provided a composition for detecting the presence of lacZ gene and/or lacZ gene activity comprising the solvent of the present invention and an effective amount of chromogenic substrate.

In accordance with the present invention, there is provided a method for inducing lac operon in screening assay, comprising the step of contacting an agar plate with at least one essential oil in a concentration sufficient to induce the lac operon.

The method in accordance with a preferred embodiment of the present invention, the lac operon being induced in one selected from the group consisting of *E. Coli, Bacillus subtilis*, phage, or in situ tissues.

In accordance with the present invention, there is provided a method for detecting the presence of bacteria, comprising the step of contacting an agar plate with at least one essential oil in a concentration sufficient to induce detection of the bacteria.

For the purpose of the present invention the following terms are defined below.

The term "chromogenic substrate" is intended to mean a substrate that produces a color when contacted with an appropriate reagent. The chromogenic substrate can be one of, but not limited to, X-Gal and IPTG.

All references herein are hereby incorporated by reference.

DETAILED DESCRIPTION OF THE INVENTION

Figure 1:
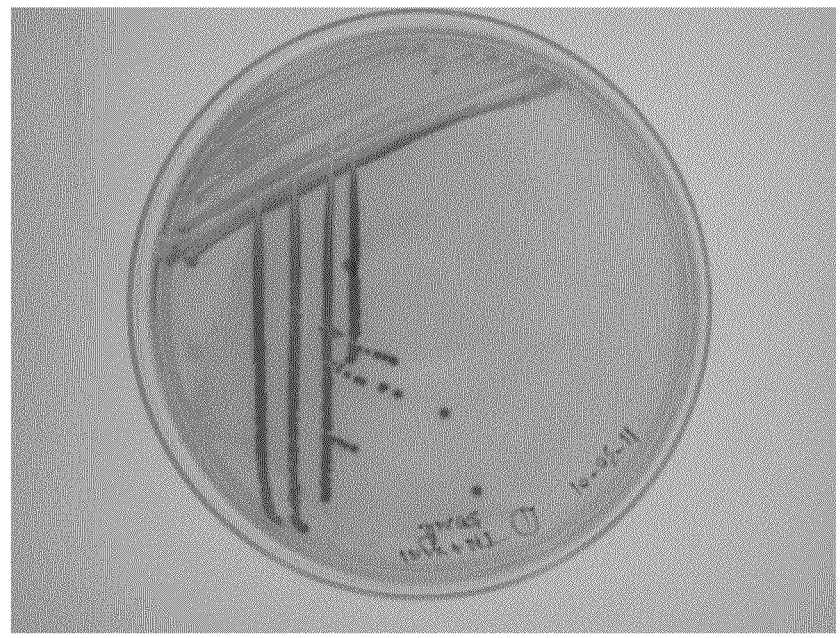
FIG. 1 illustrates a bacterial culture exhibiting a strong blue color indicative of lac operon induction without the presence of IPTG when X-gal dissolved in essential oils.

In accordance with the present invention, there is provided non-toxic solvents for dissolving and stabilizing enzyme substrate used in screening assays.

One enzyme substrate widely used is X-gal, which is a dipolar molecule having the formula I:
5-Bromo-4-chloro-3-indoxyl-beta-D-galactopyranoside

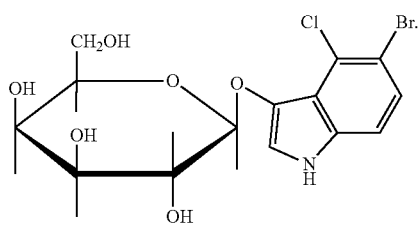

The X-gal solutions prepared with a non-toxic dipolar solvent of the present invention, for example 1-Methylpyrrolidone (NMP), N'-dimethyl propylene urea (DMPU), Propylene carbonate (PC), essential oils or a combination of these, are very stable. In solution at 4° C., the X-gal will keep its activity for more than 6 months. If used to be poured in agar plates containing the proper antibiotic, these plates will remain active and usable for at least 3 months.

As an example of its non-toxicity, NMP is known as rapidly absorbed and eliminated. It is currently used intravenously in horses as a preanaesthetic. It is also used as an excipient in topical pharmaceutical formulations in human medicine and in cosmetics.

Essential oil mixes can be used to create a dipolar environment allowing X-gal dissolution. For instance, a combination of citrus extracts, pine terpenoids, limonene and linseed oil was shown to create an environment allowing the proper dissolution of X-gal.

Non-toxic micro emulsions can also be used to dissolve X-gal. A micro emulsion is a thermodynamically stable dispersion of one liquid phase into another, stabilized by an interfacial film of surfactant. This dispersion may be either oil-in-water or water-in-oil. Micro emulsions are typically clear solutions, as the droplet diameter is approximately 100 nanometers or less. The interfacial tension between the two phases is extremely low. Emulsions are in contrast unstable, the suspended droplets will eventually agglomerate and the dispersed phase will phase separate. Emulsion droplet sizes are much larger, typically one micron or more, resulting in a cloudy or milky dispersion. The nature of an emulsion may depend on the mixing of the ingredients and the amount of energy put into the mixing process.

A combination of essential oil was extracted with chloroform in order to remove part of the oil phase, and create a semi-precipitated emulsion. For example, 20 ml of citrus extract, pine terpenoids, limonene oils and linseed oil was mixed with 20 ml of Chloroform by vigorously shaking in a 50 ml falcon tube. The resulting mix was allowed to let stand for approximately one day, and then the upper phase was transferred to a 15 ml falcon tube. The obtained phase is a milky emulsion. It dissolves X-gal very well. If we let stand the milky phase for approximately one week, it will show the development of 5 distinct phases. Isolating each phase, it was interesting to observe that only phase #2, the milky subphase, then still an emulsion, can be used as an active solution to dissolve X-gal. The active phase is yellow milky cloudy in appearance. Using 500 µl completely dissolve 0.01 g of X-gal; however, it gives a very opaque and viscous solution in appearance.

Micro emulsions are proper to create dipolar environment allowing a complete dissolution of X-gal. A mixture of oil, egg yolk or lecithine and acetic acid was sufficient to dissolve X-gal and show blue bacteria when used for its function as spread on an agar surface. Linseed oil, which has an average composition of different fatty acids (C16:0 palmitic acid 4-9%, C18:0 stearic acid 2-4%, C18:1 oleic acid 14-39%, C18:2 linoleic acid 7-19%, C18:3 linolenic acid 35-66%) is a known carrier for lipophilic molecules (as essential oils) and can act as a compound of the oily phase of the emulsion.

A micro emulsion is ideally made of a non-polar liquid mixed with a polar liquid in the presence of a surfactant or amphiphile, which is ideally a molecule carrying both polar and non-polar charges. In our situation, the surfactant, or amphiphilic molecule is X-gal. The role of the surfactant is to reduce the interfacial tension between two partially miscible or immiscible fluids below that obtained when no surfactant is present.

As shown in Table 1, variation in the composition of the microemulsion has an impact on the temperature flash point, which is a concern for transportation purposes.

TABLE 1

| X-Gal with | Flash point (° C.) |
| --- | --- |
| 10% water/90% NMP | >93 |
| 5% water/95% NMP | 88 |
| 1% seapine/10% water/89% NMP | 76 |
| 1% seapine/99% NMP | 73 |
| 10% seapine/90% NMp | 47.5 |

As well, IPTG is a usual and relatively essential addition to the cloning process. Omitting IPTG from the growth medium will decrease the expression level from plac, blue/white selection is usually not possible in the absence of IPTG. E. coli lac operon consists of a promoter, a transcriptional regulatory site called the operator (O), a CAP binding site (c), and three structural genes (lacZ, lacY and lacA) that are transcribed as a single polycistronic mRNA. Transcription of the lac operon is regulated by the lac repressor protein (lad) which is encoded on a gene physically linked to the lac operon. lac operon inducers, such as IPTG, inactivate the lac repressor protein resulting in transcriptional de-repression of the lac operon. It is possible to artificially induce the lac operon using a nonmetabolizable allolactose analogue, isopropylthiogalactoside (IPTG), which binds to the lac repressor protein.

It is shown here that essential oils are replacing IPTG to induce the lac operon. It was found that compositions comprising essential oils not only dissolves X-gal, but also enhances the blue color without the need of IPTG. Among different tested essential oils, the most interesting alternative to IPTG is a small amount of the essential oil Sea Pine. Other essential oils extracted from spruce, pine or other conifers are also candidate to replace IPTG. Using such oil instead of IPTG represents different benefits, being non-toxic, all natural, easily biodegradable, low cost and most importantly, already as a liquid solution, ready to use.

Monoterpenes and sesquiterpenes were shown to be successful in dissolving X-gal and replacing IPTG in screening clones using the blue/white X-gal selection method.

In addition to X-gal, it is also possible to dissolve IPTG with the same solutions for cloning with bacterial systems needing that stimulation (see Table 2 for examples). These same solutions allow stable dissolution of Ampicillin, tetracycline and Chloramphenicol, providing an approach wherein a complete solution is available to the user. To dissolve Kanamycin, a solution with a base of micelles in aqueous solution is essential.

TABLE 2

| Strain | (lacZ)M15 | lacIq | F' | Cam R | Kan R | Str R | Tet R | Comments |
|---|---|---|---|---|---|---|---|---|
| DH5-alpha | x | | | | | | | Invitrogen: (lacZYA)U169 |
| DH5-alpha E | x | | | | | | | Invitrogen; (lacZYA)U169 |
| DH5-alpha F' | x | | x | | | | | Invitrogen; (lacZYA)U169 |
| DH5-alpha T1R | x | | | | | | | Invitrogen; (lacZYA)U169 |
| DH10B | x | | | | | | | Invitrogen |
| DH10Bac | x | | | | | | | Invitrogen; for producing recombinant baculovirus molecules |
| DH10B T1 R | x | | | | | | | Invitrogen |
| GeneHogs | x | | | | | | | Invitrogen; D10B derivative |
| INV-alpha F' | x | | x | | | | | Invitrogen, (lacZYA)U169 |
| JM83 | x | | | | | x | | ATCC 35607 |
| Select 96 | x | | | | | | | Promega |
| TB1 | x | | | | | x | | NEB; comes with pMAL system |
| TOP10 | x | | | | | | | Invitrogen |
| TOP10/P3 | x | | | x | x | | x | Invitrogen; AMP R |
| ABLE C | x | x | x | | x | | x | Stratagene; lower plasmid copy number |
| ABLE K | x | x | x | | x | | x | stratagene; lower plasmid copy number |
| AD494 | | | | | | | | |
| BB4 | x | x | x | | | | x | =LE392.23 |
| BMH 71-18 mutS | x | x | x | | | | x | |
| DH5-alpha F' IQ | x | x | x | | x | | | Invitrogen |
| DH-alpha FT | x | x | x | | | | x | Invitrogen; (lacZYA)U169 |
| DH11S | x | x | x | | | | | Invitrogen; mainly for ssDNA production with phagemid/m13 |
| DH12S | x | x | x | | | | x | Invitrogen |
| Electro Ten blue | x | x | x | | x | | x | Stratagene |
| ER1727 | x | x | x | | | x | x | NEB |
| ER2267 | x | x | x | | | | | NEB |
| ER2738 | x | x | x | | | | | NEB |
| INV110 | x | x | | | | x | x | Invitrogen; to produce umethylated DNA |
| JM101 | x | x | x | | | | | ATCC33876 |
| JM103 | x | x | x | | | x | | ATCC 39403 |
| JM105 | x | x | x | | | x | | ATCC47016 |
| JM107 | x | x | x | | | | | ATCC47014 |
| JM109 | x | x | x | | | | | ATCC 53323; to maintain F' |

TABLE 2-continued

| Strain | (lacZ)M15 | lacIq | F' | Cam R | Kan R | Str R | Tet R | Comments |
|---|---|---|---|---|---|---|---|---|
|  |  |  |  |  |  |  |  | grow on M9 with 1 mM thiamine |
| JM110 | x | x | x |  |  | x |  | ATCC 47013 |
| NM522 | x | x | x |  |  |  |  | ATCC 47000 |
| NM527 |  |  |  |  |  |  |  |  |
| SCS110 | x | x | x |  |  | x |  | Stratagene |
| Solo Pack gold | x | x | x | x |  |  | x | Stratagene |
| SOLR | x | x | x |  | x |  |  | Stratagene; excision assist strain |
| Stbl4 | x | x | x |  |  |  | x | Invitrogen; to clone unstable DNA |
| SURE | x | x | x |  | x |  | x | Stratagene |
| SURE-2 | x | x | x | x | x |  | x | Stratagene |
| TG1 | x | x | x |  |  |  |  |  |
| TKX1 | x | x | x |  | x |  | x | Stratagene; for prot production |
| TOP10 F' | x | x | x |  |  | x | x |  |
| W3110 |  |  |  |  |  |  |  |  |
| XL1-Blue | x | x | x |  |  |  | x | Stratagene |
| XL1-Blue MRF' | x | x | x |  |  |  | x | Stratagene |
| XL1-Blue MRF' Kan | x | x | x |  | x |  | x | Stratagene |
| XL2-Blue | x | x | x | x |  |  | x | Stratagene |
| XL2-Blue MRF' | x | x | x | x |  |  | x | Stratagene |
| XL10gold | x | x | x | x |  |  | x | Stratagene |
| XL10gold Kan R | x | x | x |  | x |  | x | Stratagene |
| XL mutS Kan S | x | x | x |  |  |  | x | Stratagene |
| XL mutS Kan R | x | x | x |  | x |  | x | stratagene |
| XLOLR | x | x | x |  |  |  | x | Stratagene; excision assist strain |
| XPORT | x | x | x |  |  |  |  |  |
| G1698 | x |  |  |  |  |  |  |  |
| C1724 | x |  |  |  |  |  |  |  |
| 96 pack gold | x | x | x | x |  |  | x |  |
| EC100 | x |  |  |  |  |  |  | Epicentre; pIndigo |
| EC300 | x |  |  |  |  |  |  | Epicentre; copy control BAC |
| CC300 | x |  |  |  |  |  |  | Epicentre; copy control BAC |
| EPI100 | ? | ? |  |  |  |  |  | Epicentre; fosmid |
| EPI300 | ? | ? |  |  |  |  |  | Epicentre; fosmid |
| AG1 |  |  |  |  |  |  |  | DH1 derivative |
| BL21 (DE3) |  |  |  |  |  |  | x | for prot expression; some also Cam R or Kan R |
| BNN93 |  |  |  |  |  |  |  |  |
| C600 |  |  |  |  |  |  |  | ATCC 23724 |
| CJ236 |  |  | x | x |  |  |  |  |
| DB3.1 |  |  |  |  |  |  |  | Invitrogen; for propagating vector with ccdB gene |
| DH1 |  |  |  |  |  |  |  | ATCC 33849 |
| DH5 alpha MCR |  |  |  |  |  |  |  | Invitrogen; (lacZYA)U169 |

In a preferred embodiment of the present invention, individual LB plates are prepared adding 100 µl of X-gal solution to the surface of a LB plate being at room temperature and spreading evenly across the surface. The plate is dried before use. X-gal containing LB+Amp plates are stable for up to 90 days when stored at 4° C.

Batches can be prepared by aseptically adding X-gal solution directly to melted LB agar (temperature 50° C.). 100 µl of the solution should be used for every Petri dish. For example, for each 500 ml add 2000 µl of X-gal solution. Mix well (for 3 to 5 minutes) and pour as you normally would. Let cool. X-gal LB plates are stable for at least 3 months when stored at 4° C. X-gal can be added before or after the addition of selective antibiotics to the medium. For best mixing results, a magnetic stir bar should be added during the autoclaving process or a sterile magnetic stir bar could be ascetically added after autoclaving.

In a preferred embodiment of the present invention, X-gal solution is prepared as follow:

NMP or DMPU Only

Add 7 ml of either NMP or DMPU to 1 gram of X-gal. Stir until dissolved and bring to 10 ml with NMP or DMPU (whichever is already used).

NMP or DMPU with Essential Oil

Add 3.5 ml of either NMP or DMPU to 1 gram of X-gal. Stir until dissolved and bring to 5 ml with NMP or DMPU (whichever is already used). Mix with 5 ml of essential oil until thoroughly mixed.

NMP/Methanol Solution

Add 7 ml of either NMP or DMPU to 1 gram of X-gal and stir until dissolved. Bring to 10 ml with NMP or DMPU (whichever is already used). Add 90 ml of methanol and mix thoroughly.

Example 1

Essential Oils as Solvent and IPTG Replacement

Using 0.01 g X-gal in 500 µl of TURPENOID NATURAL® (comprising a combination of citrus extracts, pine terpenoids, limonene and linseed oil) provides excellent dissolution of X-gal and without affecting bacterial growth. It also provides a strong blue color without the need of IPTG, as shown in FIG. 1.

Example 2

Dissolution of X-gal 10 mg of X-gal powder were successfully dissolved in the solvents described in the Table 3 below.

TABLE 3

| Mix | T1– |
|---|---|
| Citrus lemon/*Citrus sinensis* | 700 µl |
| *Pinus pinaster* | 300 µl |
| Mix | T2– |
| *Cupressus sempervirens* | 50 µl |
| Pinene (Sigma) | 50 µl |

TABLE 3-continued

| Campher oil | 100 µl |
|---|---|
| *Citrus sinensis* | 800 µl |
| Mix | T3– |
| NMP | 100 µl |
| Methanol (only to increase total volume): | 900 µl |
| % NMP: | 10% |
| Mix | T4– |
| PC | 200 µl |
| Methanol (only to increase total volume): | 400 µl |
| % PC: | 33% |

Example 3

Dissolution in NPM and NMP/Methanol

A 10× X-gal/NMP solution could be stored at −20° C. without freezing. Over time, the solution will take a very pale yellow color that does not seem to darken over time. A 10× X-gal/NMP solution is easily diluted to 1× in anhydrous methanol or 95% ethanol. When diluted in methanol or ethanol, the solution will not freeze.

When the 1× X-gal/NMP/methanol is stored for 16 weeks at 4° C., there is no loss in X-gal activity as measured by applying 100 µl to a LB plate, streaking *E. coli* pUC19 transfectant, incubation at 37° C. and examination for blue colonies after 16 hours.

Tables 4 and 5 are showing the results obtained by testing the activity of X-gal in solution with different solvent on a weekly basis. In Table 4, the tested solutions were stored at 4° C. At weekly intervals, 100 µl was applied to an LB+Amp plate and streaked with *E. coli* containing pUC19. The plate was incubated overnight at 37° C. The following morning the plate was examined for blue colonies. In Table 5, LB+Amp plates were prepared and stored at 4° C. At weekly intervals, a plate was removed and streaked with *E. coli* containing pUC19. The plate was incubated at 37° C. overnight. The blueness of the colonies was then scored.

TABLE 4

Weekly Testing of X-gal/NMP/Methanol solution

| Week | Test Results |
|---|---|
| 0 | + |
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |

TABLE 4-continued

Weekly Testing of X-gal/NMP/Methanol solution

| Week | Test Results |
|---|---|
| 19 | + |
| 20 | + |

TABLE 5

Weekly testing of X-gal/NMP or X-gal/NMP/oil

| Date | NMP plate | Oil + NMP plate |
|---|---|---|
| 0 | + | + |
| 1 | + | + |
| 2 | + | + |
| 3 | + | + |
| 4 | + | + |
| 5 | + | + |
| 6 | + | + |
| 7 | + | + |
| 8 | + | + |
| 9 | + | + |
| 10 | + | + |
| 11 | + | + |
| 12 | + | + |
| 13 | + | + |
| 14 | + | + |

Example 4

Dissolution with Essential Oils

It was shown that when X-gal was first dissolved in NMP, mixed one to one with essential oil, and then diluted in methanol to 10 mg/ml the mixture would ultimately yield colonies that are darker blue than when X-gal is made up in dimethylformamide.

This work was repeated and expanded to include other essential oils. The oils tested were: Natural Orange Terpene Solvent (Eco-House); Blue Gum Eucalyptus Organic (Divine Essense); Atlas cedarwood (Pranarom); Sea Pine Turpentine (Pranarom) and Natural Turpenoid.

In this experiment, a 100 mg/ml solution of X-gal in NMP was prepared. A one to one mix with each essential oil was then made using this solution. The net X-gal concentration is now 50 mg/ml. This solution was then dilute 5× with 100% methanol such that the final concentration of X-gal is 10 mg/ml. One hundred microliters of this solution is then applied per LB plate.

As a control, 50 µl of a 20 mg/ml solution of X-gal dissolved in dimethylformamide was applied to one LB plate.

*E. coli* containing pUC19 was streaked onto each "X-gal spread" LB plate for isolated colonies. The plates were incubated at 37° C. overnight. After incubation, the growth on each X-gal plate was scored for blueness. The ranking was as follows (least blue to most blue): A (least); B and X-gal/DMF; C, D and E (most blue).

The results showed that when either Atlas Cedarwood, Sea Pine Turpenine or Natural Turpenoid were mixed with X-gal/NMP/methanol there was an enhanced blueness of the *E. Coli* pUC containing bacteria.

During assays with Sea Pine Turpentine, the amount of Sea Pine Turpentine added to the X-gal/NMP solution was serially diluted one in two four times, mixed with methanol and then spread onto LB plates. The amount of X-gal added to each plate was the same. The plates were then streaked with *E coli* containing pUC19 and incubated overnight.

An examination of the plates showed that the bluest colonies were those obtained with the original amount of Sea Pine Turpentine gave the deepest blue color.

In the previous experiments, the final X-gal concentration was 10 mg/ml. The concentration of X-gal was reduced to 7.5, 5 and 2.5 mg/ml. Plates were prepared and streaked. The net result was that there was a significant drop in blue coloration when the X-gal was dropped from 7.5 to 2.5 mg/ml. In a preferred embodiment of the present invention, X-gal is in a concentration of 10 mg/ml.

Figure 2:
FIG. 2 illustrates the results of plating a ligation/transformation onto LB plates containing X-gal dissolved in dimethylformamide (DMF)
Figure 3:
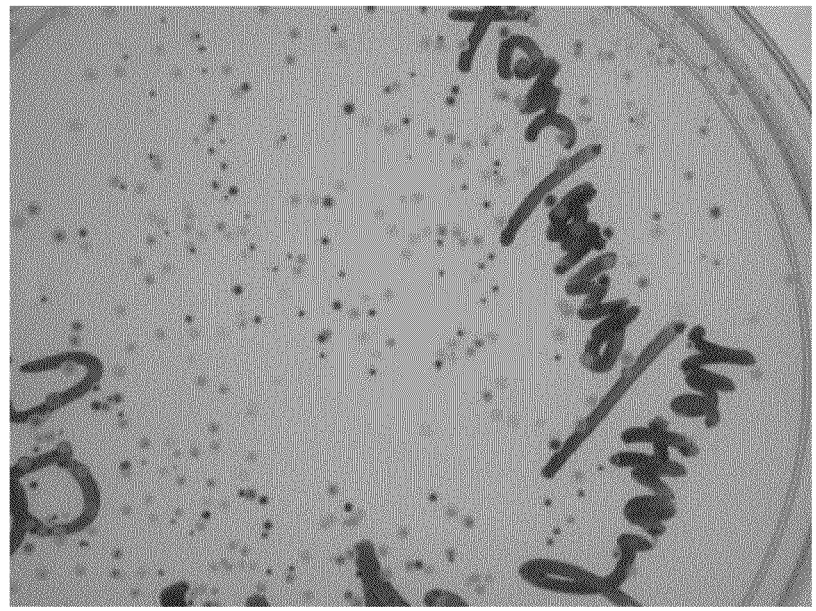
FIG. 3 illustrates the results of plating a ligation/transformation onto LB plates containing X-gal dissolved in NMP and methanol.
Figure 4:
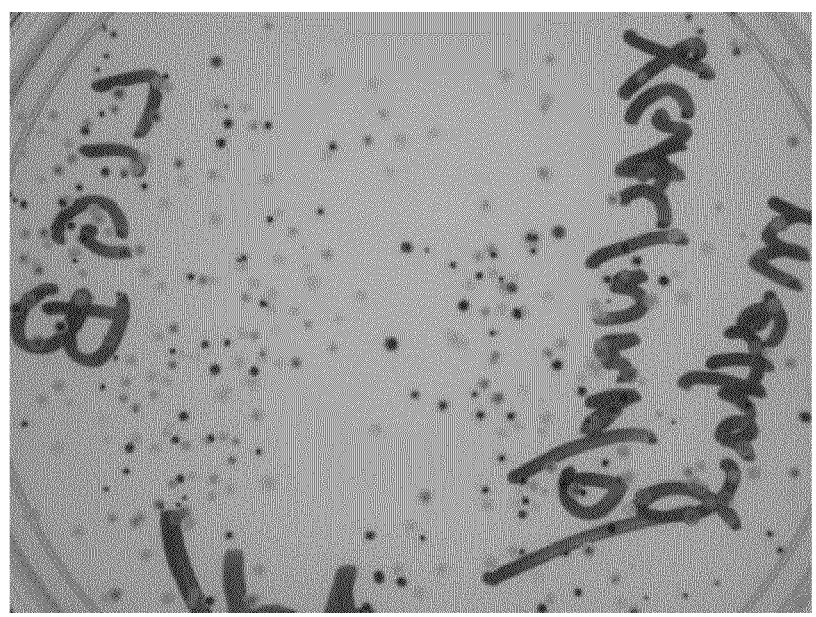
FIG. 4 illustrates the results of plating a ligation/transformation onto LB plates containing X-gal dissolved in NMP, sea pine turpentine and methanol.

Ligation assays were performed using lambda DNA digested with PstI and pUC19 digested with PstI and CTAP treated. The completed ligation was transformed into DH5α and plated onto LB plates containing:
(a) X-gal dissolved in Dimethylformamide
(b) X-gal dissolved in NMP and methanol
(c) X-gal dissolved in NMP, Sea Pine Turpentine and methanol The plates were incubated overnight. The results for a, b and c are shown in FIGS. 2, 3 and 4, respectively. For all three plating, there were both white and blue colonies. Moreover, it is shown that the blues colonies of FIG. 4 are of a more intense blue than the ones of FIGS. 2 and 3.

It is possible to incorporate X-gal directly in molten LB agar. To test this with the X-gal solution of the present invention, 500 ml of LB agar was made, autoclaved and cooled to about 50° C. To this 2 ml of a 10 mg/ml X-gal/NMP/SeaPine/methanol solution was added and mixed. Upon the addition of the X-gal solution, there was a cloudy appearance throughout the agar as it mixed. Mixing for 3 to 4 minutes did not disperse the cloudiness. However, when the plates were poured, the cloudiness dispersed upon cooling and solidification. A slight surface cloudiness was noted several hours later when the plates were inverted for incubation overnight at room temperature. However, the next day the plates looked normal.

One plate was used to streak a white and a blue colony and incubated overnight at 37° C.

Two plates were left at 25° C. These two plates served as shipping simulators. The plates were tested after 5 days and were streaked with a blue and white colony and incubated overnight.

Aging studies have been set up for the liquid product both with and without Sea Pine Turpentine. The studies conducted with the X-gal/NMP/methanol solution shown that the product is stable for 17 weeks at 4° C. with only a minor pale yellow color developing over time. This has being conducted at the same time with the X-gal/NMP/SeaPine/methanol product.

Example 5

Aging Studies

X-gal solution using NMP and/or essential oil were shown to have an improve shelf-life. Table 6 is providing life span of X-gal solutions.

TABLE 6

| Temperature | Time |
|---|---|
| 4° C. | 16 months |
| Room temperature | 4 months |
| 37° C. | 1 month |
| 65° C. | 1 month |

Moreover, it had been found that XGal Petri dishes were still active when conserved at 4° C. during as long as 12 months.

Method and Results

Figure 5:
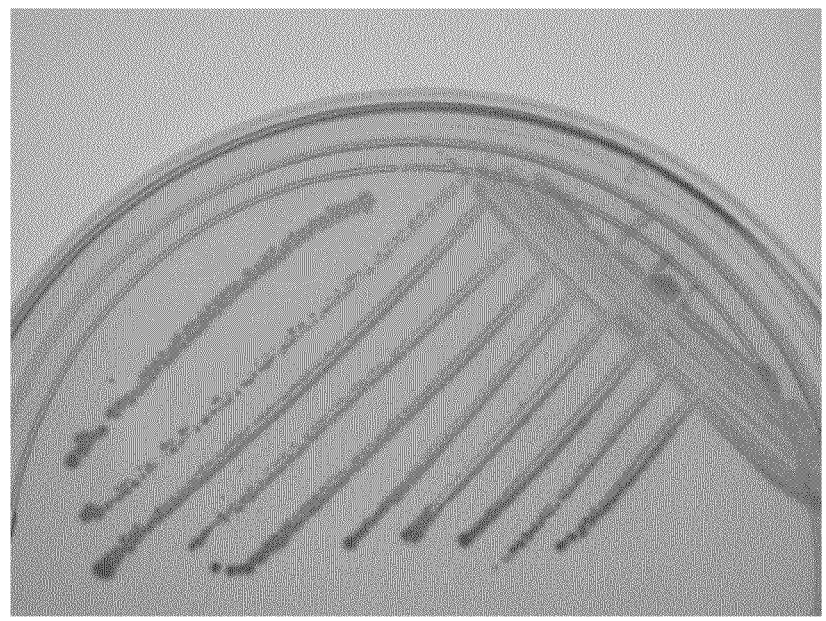
FIG. 5 illustrates the results of plating a ligation/transformation onto LB plates containing X-gal solution aged of 16 months.

Longest-term recipe is 1 Jun. 2002 in amber bottles and stored at 4° C. The recipe is 10% NMP and 90% methanol. The solution was last test Sep. 25, 2003 and found to be functioning fine (see FIG. 5). Currently, only a pale yellow color and not crystals.

X-gal containing LB plates were prepared Jul. 30, 2002. Two sets of plates were poured and stored at 4° C. only. The first set was X-gal dissolved in NMP then an equal volume of natural turpenoid extract was added followed by ethanol. The final X-gal concentration in the solution was 10 mg/ml. Ampicillin prepared in water was added separately to the molten agar before pouring.

Each week one plate was removed, streaked with pUC/DH5α and DH5α and incubated at 37° C. overnight. During the course of the experiment, the streaked pUC/DH5α always turned blue and the DH5α did not grow. Up until Jul. 30, 2003, both Ampicillin and X-gal were functioning.

Tables 7-9 provide results from more aging studies performed with solutions in accordance with the present invention

TABLE 7

10% NMP

| Main Ingredients | May 12 | June 3 | June 9 | June 13 | June 27 | July 8 | Aug 5 | Aug 15 | Sept 22 |
|---|---|---|---|---|---|---|---|---|---|
| X-gal (ethanol) May 5, 2003 | No crystals, clear solution, Ok | Clear, no crystals | Clear, no crystals | Yellow, no crystals | Yellow, no crystals ok | Yellow, no crystals ok | Yellow color, ok | Slightly yellow, no crystals ok | Slightly yellow, no crystals ok |
| X-gal (methanol) May 1, 2003 | No crystals, clear solution Ok | Clear, no crystals | Clear, no crystals ok | Clear, no crystals ok | Clear, no crystals ok | Clear, no crystals ok | Clear, no crystals ok | Clear, no crystals | Clear, no crystals |
| Ampicillin + X-gal May 6, 2003 | No crystals, slight yellow color Ok ok | Yellow, No crystals, Ok ok | yellow color, no crystals | yellow color, no crystals Ok ok | yellow, no crystals Ok ok | Yellow, no crystals Ok ok | Yellow, no crystals, Ok ok | Yellow, no crystals Ok ok | Yellow, no crystals Ok ok |
| Amp in NMP + X-gal May 15, 2003 | NA | Pale yellow Ok ok | Yellow, no crystals Ok, ok | Yellow, no crystals Ok, ok | Yellow, no crystals Ok, ok | Yellow, no crystals Ok ok | Yellow, no crystals Ok ok | Yellow, no crystals | Yellow, no crystals Ok Ok |
| Chloramphenicol IPTG (low) + X-gal May 5, 2003 | No crystals, clear solution Ok, ok | Pale yellow, no crystals, Ok, ok | Pale yellow, no crystals Ok ok | Pale yellow, no crystals Ok ok | Pale yellow, no crystals Ok Ok | Pale yellow, no crystals Ok ok | Pale yellow, no crystals Ok ok | Pale yellow, no crystals | Pale yellow, no crystals Ok ok |
| Chloramphenicol IPTG (high) + X-gal May 5, 2003 | No crystals, clear solution Ok, ok | Pale yellow, no crystals, Ok, ok | Pale yellow no crystals Ok ok | Pale yellow, no crystals Ok ok | yellow color, no crystals Ok ok | Pale yellow, no crystals, ok, ok | Pale yellow, no crystals, ok ok | Pale yellow, no crystals | Pale yellow, no crystals Ok Ok |
| Tetracycline* + X-gal (Apr. 4, 2003) | Yellow, no crystals, No growth of DH5α | Yellow, clear, no crystals, No growth of DH5α | Darker yellow, no crystals | Darker yellow, no crystals Ok ok | Darker yellow color, no crystals ok ok | Dark yellow, no crystals Ok ok | Dark yellow, no crystals Ok ok | Yellow, no crystals, ok ok | Yellow, no crystals, ok ok |
| Tetracycline (low) + X-gal (May 5, 2003) | Yellow, no crystals | Yellow, no crystals | Yellow, no crystals | Yellow, no crystals Ok ok | Yellow, no crystals | Yellow, no crystals | Yellow, no crystals, Ok, ok | Yellow, no crystals | Yellow, no crystals Ok Ok |
| Tetracycline (high) + X-gal (May 5, 2003) | Yellow, no crystals | Yellow, no crystals | Yellow, no crystals | Yellow, no crystals Ok, ok | Yellow, no crystals | Yellow, no crystals | Yellow, no crystals, Ok, ok | Yellow, no crystals | Yellow, no crystals Ok Ok |

TABLE 8

AGING TEST #1

| Formulations | | Start date | Aging test (# weeks) | Result | Aging test (# weeks) |
|---|---|---|---|---|---|
| DMF + X-Gal | RT | 17 Sep. 2003 | 1 week | Appearance of soln: clear, Intensity 4+ | 4 weeks |
| | −20 | mid-july-03 | ~9 weeks | Appearance of soln: clear, Intensity 4+ | ~12 weeks |
| BT lot no. 024 (25% NMP) | 65 C. | 17 Sep. 2003 | 1 week | Appearance of soln: yellow, Intensity 4+ | 4 weeks |
| | 37 C. | 17 Sep. 2003 | 1 week | Appearance of soln: light yellow, Intensity 4+ | 4 weeks |
| | RT | 21 Aug. 2003 | 5 weeks | Appearance of soln: clear, Intensity 4+ | 8 weeks |
| | 4 C. | 5 Aug. 2003 | ~7 weeeks | Appearance of soln: clear, Intensity 4+ | ~10 weeks |
| BT lot no. 004 | RT | 21 Aug. 2003 | 5 weeks | Appearance of soln: light yellow, Intensity 4+ | 8 weeks |
| | 4 C. | 18 Feb. 2003 | ~31 weeks | Appearance of soln: light yellow, Intensity 4+ | ~34 weeks |
| BT Amp, lot 019 | RT | 21 Aug. 2003 | 5 weeks | Appearance of soln: yellow, Intensity 3+ | 8 weeks |
| | 4 C. | 16 May 2003 | ~18 weeks | Appearance of soln: yellow, Intensity 3+ | ~21 weeks |

All were tested with DH5 + TrueBlue
BT lot no. 024 (25% NMP) has an intensity rated higher than others probably because the resulting evaporation made it more [ ]

TABLE 9

AGING TEST NEW FORMULATIONS

| Formulations | | Start date | Week 2 | Result | W4 (M1) |
|---|---|---|---|---|---|
| A + X-Gal/IPTG | 65 C. | 28 Sep. 2003 | 14 Oct. 2003 | Appearance of soln: VERYyellow, Intensity 3+ | 28 Oct. 2003 |
| | 37 C. | 28 Sep. 2003 | 14 Oct. 2003 | Appearance of soln: light yellow, Intensity 4+ | 28 Oct. 2003 |
| | RT | 28 Sep. 2003 | | | 28 Oct. 2003 |
| | 4 C. | 28 Sep. 2003 | 14 Oct. 2003 | Appearance of soln: clear, Intensity 4+ | 28 Oct. 2003 |
| | −20 | 28 Sep. 2003 | | | 28 Oct. 2003 |
| D + X-Gal/IPTG | 65 C. | 28 Sep. 2003 | 14 Oct. 2003 | Appearance of soln: VERYyellow, Intensity 3+ | 28 Oct. 2003 |
| | 37 C. | 28 Sep. 2003 | 14 Oct. 2003 | Appearance of soln: light yellow, Intensity 4+ | 28 Oct. 2003 |
| | RT | 28 Sep. 2003 | | | |
| | 4 C. | 28 Sep. 2003 | 14 Oct. 2003 | Appearance of soln: clear, Intensity 4+ | |
| | −20 | 28 Sep. 2003 | | | 28 Oct. 2003 |
| K + X-Gal/IPTG | 65 C. | 28 Sep. 2003 | 14 Oct. 2003 | Appearance of soln: brown-orange, Intensity 3+ | 28 Oct. 2003 |
| | 37 C. | 28 Sep. 2003 | 14 Oct. 2003 | Appearance of soln: yellow, Intensity 4+ | 28 Oct. 2003 |
| | RT | 28 Sep. 2003 | | | 28 Oct. 2003 |
| | 4 C. | 28 Sep. 2003 | 14 Oct. 2003 | Appearance of soln: clear, Intensity 4+ | 28 Oct. 2003 |
| | −20 | 28 Sep. 2003 | | | 28 Oct. 2003 |
| BT PLUS lot no. 028, 25% NMP | 65 C. | 28 Sep. 2003 | 14 Oct. 2003 | Appearance of soln: greenish-brown, Intensity 3+ | 28 Oct. 2003 |
| | 37 C. | 28 Sep. 2003 | 14 Oct. 2003 | Appearance of soln: light yellow, Intensity 4+ | 28 Oct. 2003 |
| | RT | 28 Sep. 2003 | | | 28 Oct. 2003 |
| | 4 C. | 28 Sep. 2003 | 14 Oct. 2003 | Appearance of soln: clear, Intensity 4+ | 28 Oct. 2003 |
| | −20 | 28 Sep. 2003 | | | 28 Oct. 2003 |
| DMF + X-Gal/IPTG | 65 C. | 28 Sep. 2003 | 14 Oct. 2003 | Appearance of soln: orange, Intensity --- | |
| | 37 C. | 28 Sep. 2003 | 14 Oct. 2003 | Appearance of soln: clear, Intensity 4+ | 28 Oct. 2003 |
| | RT | 28 Sep. 2003 | | | 28 Oct. 2003 |
| | 4 C. | 28 Sep. 2003 | | | 28 Oct. 2003 |
| | −20 | 28 Sep. 2003 | 14 Oct. 2003 | Appearance of soln: clear, Intensity 4+ | 28 Oct. 2003 |
| DMSO + X-Gal/IPTG | 65 C. | 28 Sep. 2003 | 14 Oct. 2003 | Appearance of soln: greenish-brown, Intensity --- | |
| | 37 C. | 28 Sep. 2003 | 14 Oct. 2003 | Appearance of soln: light yellow, Intensity 4+ | 28 Oct. 2003 |
| | RT | 28 Sep. 2003 | | | 28 Oct. 2003 |
| | 4 C. | 28 Sep. 2003 | | | 28 Oct. 2003 |
| | −20 | 28 Sep. 2003 | 14 Oct. 2003 | Appearance of soln: clear, Intensity 4+ | 28 Oct. 2003 |

Test 14 oct was done with DH5 + TrueBlue
Test 28 oct was done with XL1 + PUC (also solutions are 65 C. were rought back to 1400 uL)

Figure 6:
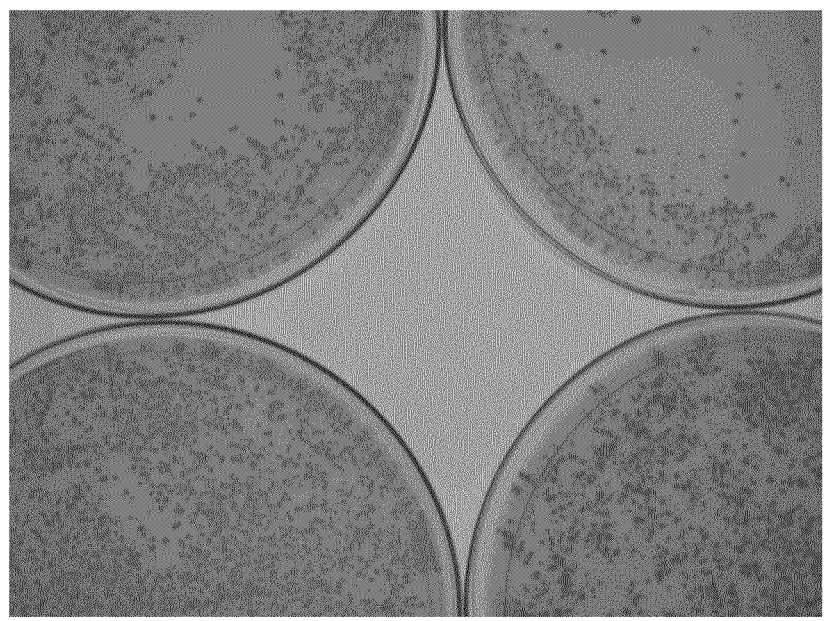
FIG. 6 illustrates the aging of LB plates at 4° C., room temperature, 37° C. and 65° C. (in the clockwise direction)

In FIG. 6, dishes from the BT lot no. 024, as described in Table 8 are illustrated. The two top left dish was conserved at 4° C., the top right dish was conserved at room temperature, the bottom left dish was conserved at 37° C. and the bottom right dish was conserved at 65° C.

Figure 7A:
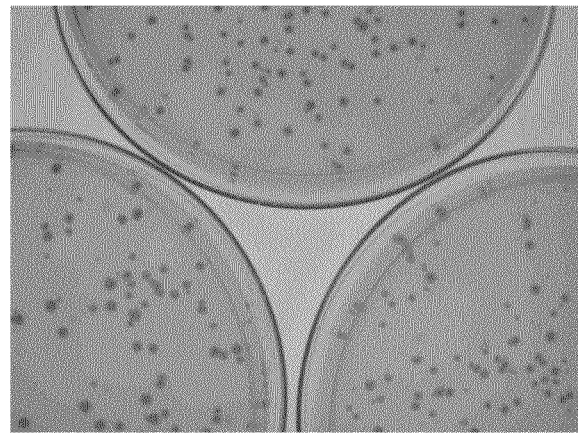
FIGS. 7A-7C illustrate LB plates after 2 weeks at various temperatures.

In FIG. 7A, dishes from the lot A, as described in Table 9, are illustrated. The top dish was conserved two weeks at 4° C., the bottom left dish was conserved two weeks at 37° C. and the bottom right dish was conserved two weeks at 65° C.

Figure 7B:
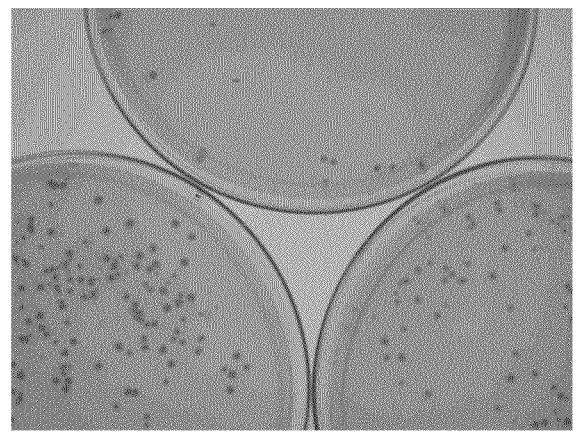

In FIG. 7B, dishes from the lot 028, as described in Table 9, are illustrated. The top dish was conserved two weeks at 4° C., the bottom left dish was conserved two weeks at 37° C. and the bottom right dish was conserved two weeks at 65° C.

Figure 7C:
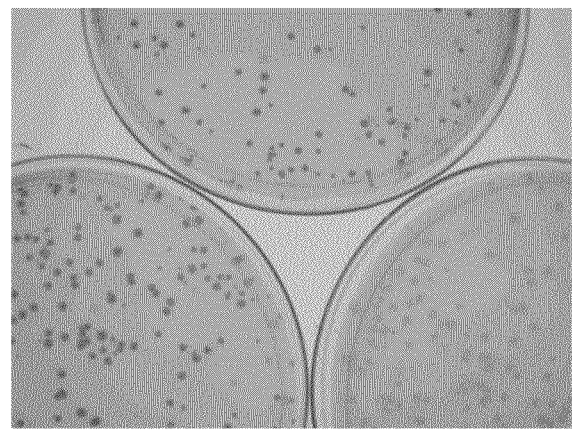

In FIG. 7C, dishes from the lot DMSO, as described in Table 9, are illustrated. The top dish was conserved two weeks at −20° C., the bottom left dish was conserved two weeks at 37° C. and the bottom right dish was conserved two weeks at 65° C.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A biochemical solvent for a chromogenic substrate for detecting presence, activity, expression, and/or non-expression of a lacZ gene, the solvent comprising a compound selected from the group consisting of 1-methylpyrrolidone (NMP), $N^1$-dimethyl propylene urea (DMPU), propylene carbonate (PC), and combinations thereof, and a lipophilic essential oil creating a dipolar environment, in a concentration sufficient to induce a lac operon, selected from the group consisting of *Abies alba, Aniba roseodora, Cedrus atlantica, Citrus aurantifolia, Citrus aurantium, Citrus bergamia, Citrus limon, Citrus paradisi, Citrus reticulata, Citrus sinensis, Cupressus sempervirens, Juniperus communis, Juniperus virginiana, Picea mariana, Pinus pinaster, Pinus sylvestris, Ravensara aromatica, Rosmarinus officinalis*, citrus extracts, pine terpenoids, conifers extracts, limonene oil, linseed oil, and combinations thereof.

2. The solvent of claim 1 where the compound is at a concentration sufficient to maintain substrate activity for more than six months in solution at 4° C.

3. The solvent of claim 1 being a microemulsion.

4. The solvent of claim 1 as a ready-to-use non-toxic liquid.

5. A composition for detecting the presence of lacZ gene comprising the solvent of claim 1 and an effective amount of a chromogenic substrate selected from the group consisting of substituted indolyl-β-D-galactoside, halo-substituted indolyl-β-D-galactoside, 5-bromo-4-chloro-3-indoxyl-β-D-galactopyranoside (X-gal), and combinations thereof.

6. A composition for detecting the presence of lacZ gene comprising
the solvent of claim 1, and
an effective amount of substituted indolyl-β-D-galactoside or halo-substituted indolyl-β-D-galactoside chromogenic substrate selected from the group consisting of 5-bromo-6-chloro-3-indolyl-β-D-galactopyranoside, 6-chloro-3-indolyl-β-D-galactopyranoside, n-methylindolyl-β-D-galactopyranoside, and 5-iodo-3-indolyl-β-D-galactopyranoside.

7. A composition for detecting presence, activity, and/or expression of a lacZ gene, the composition comprising
a chromogenic substrate to visibly indicate presence, activity, and/or expression of the lacZ gene, the substrate selected from the group consisting of substituted indolyl-β-D-galactoside or halo-substituted indolyl-β-D-galactoside;
a biochemical solvent comprising at least one solubilizing agent selected from the group consisting of 1-methylpyrrolidone (NMP), $N^1$-dimethyl propylene urea (DMPU), propylene carbonate (PC), and combinations thereof, and at least one essential oil creating a dipolar environment,
wherein the at least one essential oil is at a concentration sufficient to induce a lac operon.

8. The composition of claim 7 where the inducer is not isopropylthio-β-D-galactoside (IPTG).

9. The composition of 7 further comprising at least one antibiotic with the substrate.

10. The composition of claim 9 where the antibiotic is selected from the group consisting of ampicillin, tetracycline, chloramphenicol, kanamycin, and combinations thereof.

11. A self-contained pre-cast medium for detecting activity and/or expression or non-expression of a lacZ gene, the medium comprising an agar matrix and in or on the agar matrix
a chromogenic substrate selected from the group consisting of substituted indolyl-β-D-galactoside, halo-substituted indolyl-β-D-galactoside, and 5-bromo-4-chloro-3-indoxyl-β-D-galactopyranoside (X-gal);
a biochemical solvent comprising at least one solubilizing agent selected from the group consisting of 1-methylpyrrolidone (NMP), $N^1$-dimethyl propylene urea (DMPU), propylene carbonate (PC), and combinations thereof, and at least one lipophilic essential oil creating a dipolar environment,
wherein the essential oil is at a concentration sufficient to induce a lac operon.

12. The medium of 11 further comprising at least one antibiotic with the substrate.

13. The medium of claim 12 where the antibiotic is selected from the group consisting of ampicillin, tetracycline, chloramphenicol, kanamycin, and combinations thereof.

14. The medium of claim 11 having functional stability for at least three months 4° C.

15. The medium of claim 11 in a ready-to-use plate.

16. A composition for detecting presence, activity, expression, and/or non-expression of a lacZ gene, the composition comprising
a chromogenic substrate providing a visible indication of the presence, activity, expression, and/or non-expression of the lacZ gene,
a non-toxic microemulsion biochemical solvent selected from the group consisting of 1-methylpyrrolidone (NMP), $N^1$-dimethyl propylene urea (DMPU), propylene carbonate (PC), and combinations thereof facilitating substrate dissolution, and
at least one lipophilic essential oil creating a dipolar environment and replacing isopropylthio-β-D-galactoside (IPTG) at a concentration sufficient to induce a lac operon.

17. The composition of claim 16 as a ready-to-use liquid.

18. A composition for detecting presence, activity, expression, and/or non-expression of a lacZ gene, the composition comprising
a chromogenic substrate providing a visible indication of the presence of lacZ gene and/or lacZ gene activity;
a first phase comprising at least one solubilizing agent selected from the group consisting of 1-methylpyrrolidone (NMP), $N^1$-dimethyl propylene urea (DMPU), propylene carbonate (PC), an essential oil, and combinations thereof;
a second phase comprising sea pine turpentine in a concentration of at most 1% v/v of the composition sufficient to induce a lac operon, and
water;
the composition being a microemulsion facilitating substrate dissolution and having a flash point greater than 73° C.

19. The composition of claim 18 where the flash point is 76° C.

20. A composition comprising
a chromogenic substrate selected from the group consisting of substituted indolyl-β-D-galactoside, halo-substituted indolyl-β-D-galactoside, or 5-bromo-4-chloro-3-indoxyl-β-D-galactopyranoside (X-gal);
a 1-methylpyrrolidone (NMP) solubilizing agent; and
sea pine turpentine in a concentration sufficient to induce a lac operon;
the composition having a flash point greater than 73° C.

21. The composition of claim 20 where the substituted indolyl-β-D-galactoside or halo-substituted indolyl-β-D-galactoside is selected from the group consisting of 5-bromo-6-chloro-3-indolyl-β-D-galactopyranoside, 6-chloro-3-indolyl-β-D-galactopyranoside, n-methylindolyl-β-D-galactopyranoside, and 5-iodo-3-indolyl-β-D-galactopyranoside.

22. The composition of claim 20 having about 1% sea pine turpentine.

23. The composition of claim 20 having a flash point of 76° C.

24. The composition of claim 20 having about 89% NMP.

25. The composition of claim 20 being transport safe.

26. The composition of claim 20 lacking methanol.

* * * * *

UNITED STATES PATENT AND TRADEMARK OFFICE
CERTIFICATE OF CORRECTION

| | | |
|---|---|---|
| PATENT NO. | : 9,046,495 B2 | Page 1 of 1 |
| APPLICATION NO. | : 13/958867 | |
| DATED | : June 2, 2015 | |
| INVENTOR(S) | : Sevigny et al. | |

It is certified that error appears in the above-identified patent and that said Letters Patent is hereby corrected as shown below:

On the title page item (73),
Assignee reads:

"PIERCE BIOTECHNOLOGY, INC."

Assignee should read:

-- FISHER SCIENTIFIC COMPANY L.L.C. --

Signed and Sealed this
Tenth Day of May, 2016

Michelle K. Lee
*Director of the United States Patent and Trademark Office*